United States Patent [19]
Bojsen et al.

[11] Patent Number: 5,608,151
[45] Date of Patent: Mar. 4, 1997

[54] ANTI-MICROBIAL PROTEINS

[75] Inventors: Kirsten Bojsen, Allerød; Karsten M. Kragh, Frederiksberg; Jørn D. Mikkelsen, Hvidovre; Klaus K. Nielsen, Frederiksberg; John E. Nielsen, Copenhagen S, all of Denmark

[73] Assignee: Sandoz Ltd., Basel, Switzerland

[21] Appl. No.: 420,526

[22] Filed: Apr. 12, 1995

Related U.S. Application Data

[62] Division of Ser. No. 209,923, Feb. 22, 1994, abandoned.

[30] Foreign Application Priority Data

Feb. 24, 1993 [GB] United Kingdom .................. 9303725

[51] Int. Cl.$^6$ .............................. A01H 5/00; C12N 15/29; C12N 15/82
[52] U.S. Cl. .................. 800/205; 800/250; 800/DIG. 56; 536/23.6; 435/69.1; 435/172.3; 435/252.3
[58] Field of Search .................................... 800/205, 250, 800/DIG. 56, DIG. 9; 536/23.6; 530/370; 435/69.1, 172.3, 252.3; 514/2, 12

Primary Examiner—David T. Fox
Assistant Examiner—Elizabeth F. McElwain
Attorney, Agent, or Firm—Lynn Marcus-Wyner

[57] ABSTRACT

Anti-microbial proteins isolated from sugar beet, wherein the anti-microbial proteins exclude chitinases and glucanases. Said proteins include a pure protein selected from those depicted in SEQ ID Nos 2, 5 and 8, or a functionally equivalent analogue thereof in which one or more amino acids have been added, substituted or removed without substantially reducing the protein's anti-microbial activity, or mixtures of such proteins or analogues. A synergistic anti-fungal effect is observed if at least one of the AX proteins is combined with a WIN protein. The invention also provides recombinant DNA comprising a sequence encoding a protein according to the invention, a vector comprising said DNA and transformed plants comprising said DNA. The invention further provides an anti-microbial composition containing one or more of the said proteins, and a process for combatting fungi or bacteria which comprises exposing them to said proteins or compositions.

19 Claims, 10 Drawing Sheets

ANTI-MICROBIAL PROTEINS

This is a divisional of application Ser. No. 08/209,923, filed on Feb. 22, 1994, now abandoned.

BACKGROUND OF THE INVENTION

The present invention relates to anti-microbial proteins isolated from sugar beet.

An anti-microbial protein includes a protein (alone or in combination with another material) which is toxic or growth inhibitory under any circumstances to any micro-organism, including bacteria, viruses and particularly fungi. Such anti-microbial proteins include those that exhibit anti-microbial activity upon contact with a micro-organism and those that are anti-microbial as a consequence of assimilation or respiration thereof.

According to the present invention there is provided anti-microbial proteins isolated from sugar beet, wherein the anti-microbial proteins exclude chitinases and glucanases.

It is preferred that the sugar beet has been infected with a fungus of the genus Cercospora, and more particularly preferred that the proteins have been isolated from the leaves of sugar beet infected with *Cercospora beticola*.

The invention also includes a pure protein selected from those depicted in SEQ ID Nos 2, 5 and 8, or a functionally equivalent analogue thereof in which one or more amino acids have been added, substituted or removed without substantially reducing the protein's anti-microbial activity; or mixtures of such proteins or analogues.

The invention also includes a pure protein consisting of residues 80-111 in SEQ ID No. 8, or residues 29-74 in either SEQ ID No. 2 or SEQ ID No. 5, or a functionally equivalent analogue thereof in which one or more amino acids have been added, substituted or removed without substantially reducing the protein's anti-microbial activity; or mixtures of such proteins or analogues. Proteins having the amino acid sequences of residues 29-74 in SEQ ID Nos 2 and 5 are hereinafter referred to as AX 1 and AX2 respectively, and protein having the amino acid sequence of residues 80-111 in SEQ ID No. 8 is hereinafter referred to as AX3.1

Infection of plants with fungal or viral pathogens may induce a synthesis of about 10 families of homologous pathogenesis-related proteins (PR proteins) in vegetative tissues. Such PR-proteins have been classified into 5 groups. The PR-2, PR-3 and PR-5 proteins are beta-1,3-glucanase, chitinases and thaumatin-like proteins respectively. Specific functions have not been assigned to the PR-1 and PR-4 groups of proteins. The PR-4 proteins are similar to C-terminal domains of prohevein and the putative wound-induced WIN proteins of potato, thus lacking the N-terminal herein domain. "Basic counter-part of the acidic pathogenesis-related 4 group of proteins" thus includes the basic counter part of proteins similar to the C-terminal domains of prohevein and the putative wound-induced WIN proteins of potato.

SUMMARY OF THE INVENTION

It is preferred that the protein which is the basic counterpart of the said pathogenesis-related proteins is a chitin-binding WIN protein, most preferably capable of being isolated from barley grain or stressed barley leaf.

Included as a preferred embodiment of the invention is one or more of the said proteins or analogues in combination with protein which is the basic counter-part of the acidic pathogenesis-related 4 group of proteins, and in particular a chitin-binding WIN protein comprising the amino acid sequence depicted in SEQ ID No. 11, or a functionally equivalent analogue thereof in which one or more amino acids have been added, substituted or removed without substantially reducing the protein's anti-microbial and/or chitin-binding activity.

The invention still further includes the above disclosed proteins which have been synthesized in vitro from a knowledge of their amino acid sequences.

The invention still further includes pure proteins which have an amino acid sequence which is at least 55% similar to the sequence of one of the AX proteins according to the invention. It is preferred that the degree of similarity is at least 60%, more preferred that the degree of similarity is at least 70% and still more preferred that the degree of similarity is at least 80%.

In the context of the present invention, two amino acid sequences with at least 55% similarity to each other are defined by having at least 70% identical or similar amino acids residues in the same position when aligned optimally allowing for up to 4 deletions or up to 10 additions. For the purpose of the present invention:

Alanine, Serine and Threonine are similar;

Glutamic acid and Aspartic acid are similar;

Asparagine and Glutamine are similar;

Arginine and Lysine are similar;

Isoleucine, Leucine, Methionine and Valine are similar;

Phenylalanine, Tyrosine and Tryptophan are similar.

The invention still further includes recombinant DNA comprising a sequence, for example one of those depicted in SEQ ID Nos 1, 3, 4, 6, 7 or 9, which encodes one or more of the said anti-microbial proteins or analogues thereof. The recombinant DNA sequence may optionally comprise a sequence encoding protein which is the basic counter-part of the acidic pathogenesis-related 4 group of proteins as described above.

The invention also includes a DNA sequence which hybridizes under stringent hybridization conditions with the recombinant DNA sequence disclosed in the immediately preceding paragraph. "Stringent hybridization conditions" are those in which hybridization is effected at between 50° and 60° C. in 2X saline titrate buffer containing 0.1% SDS followed by merely rinsing at the same temperature but in a buffer having a reduced SSC concentration which will not affect the hybridizations that have taken place. Such reduced concentration buffers are respectively (a) 1×SSC, 0.1% SDS; or (b) 0.5×SSC, 0.1% SDS; or (c) 0.1×SSC, 0.1% SDS.

The invention further includes a vector containing said recombinant DNA sequences. Such sequences are under the control of a suitable promoter and terminator, including those controlling transcription of heat shock proteins.

The invention further includes a biological system, particularly a plant or micro-organism, which contains and enables expression of said recombinant DNA.

The invention further includes plants transformed with said recombinant DNA.

Such plants are made by known methods and include regeneration of plant cells or protoplasts transformed with the DNA of the invention according to a variety of known methods (Agrobacterium Ti and Ri plasmids, electroporation, micro-injection, micro-projectile gun etc). The transformed cells may, in suitable cases, be regenerated into whole plants in which the recombinant DNA is stably incorporated into the genome. Both monocot and dicot plants may be obtained in this way, although the latter are generally more easy to regenerate.

Examples of genetically modified plants according to the present invention include: fruits, including tomatoes, mangoes, peaches, apples, pears, strawberries, bananas, and melons; field crops such as canola, sunflower, tobacco, sugar beet, small grain cereals such as wheat, barley and rice, corn and cotton, and vegetables such as potato, carrot, lettuce, cabbage and onion.

The particularly preferred plants are sugar beet and corn.

The plants may be transformed with a recombinant DNA sequence including: a portion encoding the protein AX1 (residues 29–74 in SEQ ID No. 2) or a functionally equivalent analogue thereof in which one or more amino acids have been added, substituted or removed without substantially reducing its anti-microbial activity; or a recombinant DNA sequence including a portion encoding the protein AX2 (residues 29–74 in SEQ ID No. 5) or a functionally equivalent analogue thereof in which one or more amino acids have been added, substituted or removed without substantially reducing its anti-microbial activity; or a recombinant DNA sequence including a portion encoding the protein AX3.1 (residues 80–111 in SEQ ID NO. 8) or a functionally equivalent analogue thereof in which one or more amino acids have been added, substituted or removed without substantially reducing its anti-microbial activity; or a DNA sequence including a portion encoding a combination of two or more of these AX proteins or analogues.

The invention also includes plants transformed with the said recombinant DNA sequence, wherein the DNA sequence further encodes protein which is the basic counter-part of the acidic pathogenesis-related 4 group of proteins, in particular the chitin-binding WIN protein (residues 22–146 in SEQ ID No. 11) which may be isolated from barley grain or stressed barley leaf.

The invention further includes the progeny of such transformed plants, which progeny express the said recombinant DNA sequences, as well as the seeds of such plants and progeny.

The invention further includes protein derived from expression of the said recombinant DNA, including anti-microbial protein produced by expression of recombinant DNA within said plants.

The invention further includes an anti-microbial composition comprising one or more of the anti-microbial proteins.

The invention further includes a process for combatting fungi or bacteria which comprises exposing them to the anti-microbial proteins or to compositions comprising them.

The invention further includes an extraction process for producing the anti-microbial proteins from organic material containing them, and in particular a process which comprises submitting the material to maceration and solvent extraction. The anti-microbial proteins may then be subsequently purified by centrifugation, and chromatographies selected from the group consisting of hydrophobic interaction; anionic exchange; cationic exchange; gel filtration; and reverse phase chromatography.

It is preferred that the said extraction procedure is performed on organic matter which comprises leaves of sugar beet which is infected with *Cercospora beticola*, or a microorganism comprising recombinant DNA comprising a sequence coding for an anti-microbial protein or analogue thereof according to the present invention, or such a recombinant DNA sequence which further comprises a DNA sequence encoding protein which is the basic counter-part of the acidic pathogenesis-related 4 group of proteins. It will be appreciated that the anti-microbial protein exhibits little, if any, anti-microbial effect on the micro-organism which is the source of the organic matter referred to in the previous sentence.

The invention may be further understood by reference to the following specific description including Sequence Identifications, and Figures.

BRIEF DESCRIPTION OF THE DRAWINGS

FIG. 4A shows the morphology of *C. beticola* grown in the absence of the WIN and AX2 proteins.

Figure 1:
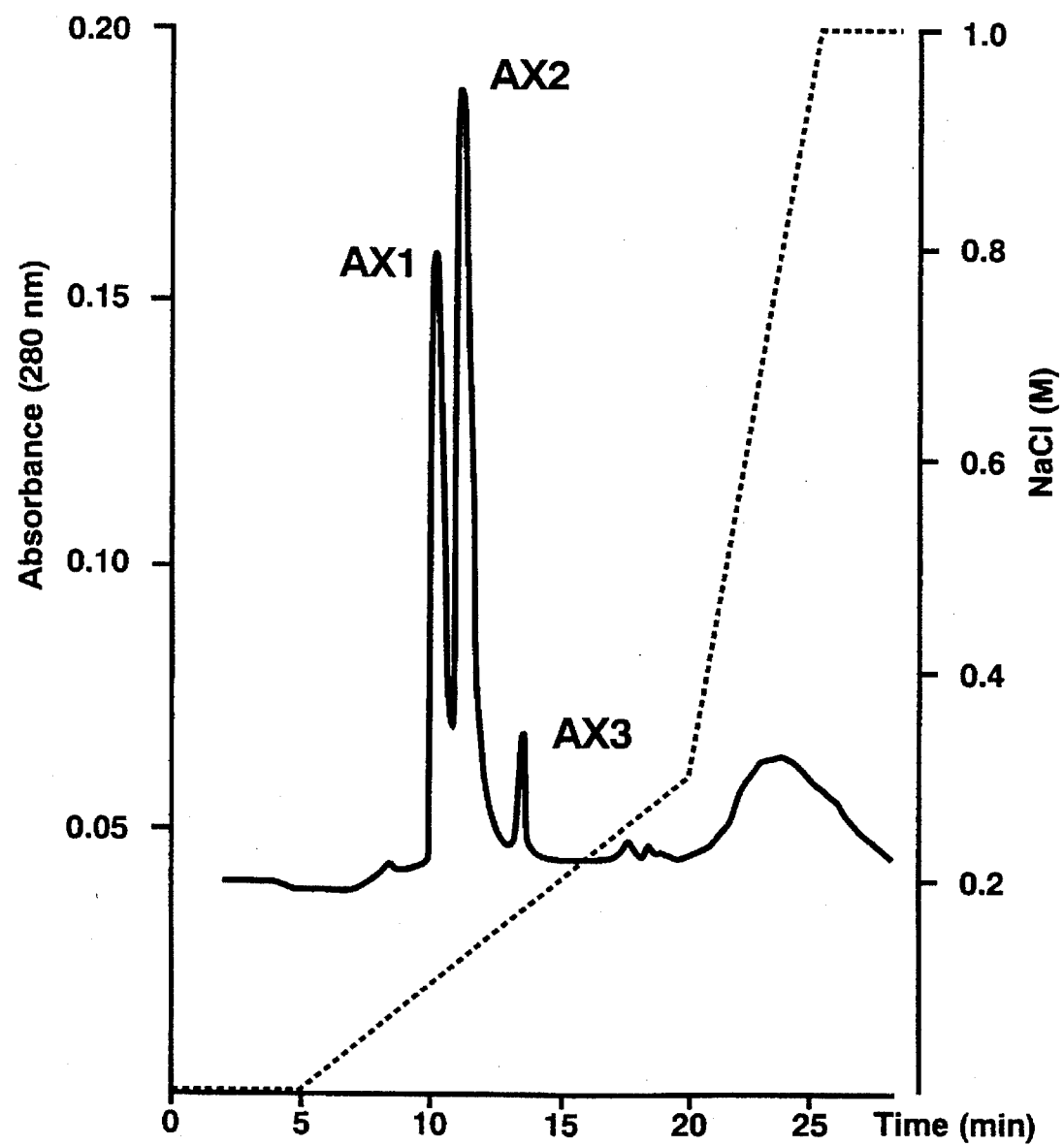
FIG. 1 shows the elution of AX 1, AX2 and AX3 proteins from a cationic Mono S column with increasing sodium chloride concentration (dotted line).

SEQ ID No 1 shows a PCR generated cDNA sequence encoding the protein AX 1 together with the signal peptide therefor. The start codon for the signal peptide is at nucleotides 40–42 and the stop codon for the AX1 protein is at positions 262–264.

SEQ ID No 2 shows the amino acid sequence of the AX1 protein together with its signal peptide. The signal peptide consists of residues 1–28 and the mature protein consists of residues 29–74.

SEQ ID No 3 shows a PCR generated cDNA sequence comprising SEQ ID No 1, except that a translation enhancing fragment (constituting nucleotides 13–79) is positioned in front of the start codon (nucleotides 82–84) in respect of the signal peptide. The sequence comprises a Pst1 restriction site at nucleotides 1–6 and a BamH1 site at nucleotides 7–12. Nucleotides 80–86 constitute an Nco1 site. The stop codon in respect of the AX1 protein is at nucleotides 304–306. Sal1 and Sph1 restriction sites are present at nucleotides 338–343 and 344–349 respectively.

SEQ ID No 4 shows a PCR generated cDNA sequence encoding the protein AX2 together with the signal peptide therefor. The start codon for the signal peptide is at nucleotides 53–55 and the stop codon for the AX2 protein is at positions 275–277.

SEQ ID No 5 shows the amino acid sequence of the AX2 protein together with its signal peptide. The signal peptide consists of residues 1–28 and the mature protein consists of residues 29–74.

SEQ ID No 6 shows a PCR generated cDNA sequence comprising SEQ ID No 4, except that a translation enhancing fragment (constituting nucleotides 13–79) is positioned in front of the start codon (nucleotides 82–84) in respect of the signal peptide. The sequence comprises a Pst1 restriction site at nucleotides 1–6 and a BamH1 site at nucleotides 7–12. Nucleotides 80–86 constitute an Nco1 site. The stop codon in respect of the AX2 protein is at nucleotides 304–306. Sal1 and Sph1 restriction sites are present at nucleotides 352–357 and 358–363 respectively.

SEQ ID No 7 shows a PCR generated cDNA sequence encoding the protein AX3.1 together with the putative signal peptide therefor. The start codon for the signal peptide is at nucleotides 23–25 and the stop codon for the AX3.1 protein is at positions 356–358.

SEQ ID No 8 shows the amino acid sequence of the unprocessed translation product encoded by the cDNA of SEQ ID No. 7. This putative preprotein includes the mature AX3.1 protein in residues 80–111.

SEQ ID No 9 shows a PCR generated cDNA sequence comprising SEQ ID No 7, except that a translation enhancing fragment (constituting nucleotides 13–79) is positioned in front of the start codon (nucleotides 82–84) in respect of the signal peptide. The sequence comprises a Pst1 restriction site at nucleotides 1–6 and a BamH1 site at nucleotides 7–12. Nucleotides 80–86 constitute an Nco1 site. The stop codon in respect of the AX3.1 protein is at nucleotides 415–417. Sal1 and Sph1 restriction sites are present at nucleotides 473–478 and 479–484 respectively.

SEQ ID No 10 shows a cDNA comprising the gene encoding the Barley WIN protein.

SEQ ID No 11 shows the amino acid sequence of the Barley WIN protein together with its signal peptide. The signal peptide consists of residues 1–21 and the mature protein consists of residues 22–146.

SEQ ID No 12 shows a PCR generated nucleotide sequence encoding the Barley WIN protein. The 5' region of the sequence comprises Pst1, BamH1 and Nco1 restriction sites. Position 62 in the original clone was a C rather than a G as presently shown. The change from C to G does not alter the amino acid sequence of the protein and was made to remove a Nco1 site at that position. The start codon in respect of the WIN protein is at nucleotides 12–14 and the stop codon at nucleotides 450–452.

SEQ ID No 13 shows essentially the nucleotide sequence given in SEQ ID No 12, except that a translation enhancing fragment (constituting nucleotides 13–79 in ID No 13) is positioned in front of the WIN gene start codon (nucleotides 82–84). The stop codon is at nucleotides 520–522.

DESCRIPTION OF THE PREFERRED EMBODIMENTS

Purification of the AX1-3 proteins from leaves of sugar beet infected with *Cercospora beticola*

AX1-3 are isolated from leaf material of sugar beet, cvs Turbo, or Rhizor naturally infected with *C. beticola*. Leaves carrying 50 or more necrotic lesions are picked in a field in Italy and stored at 4° C. until extraction. All steps are performed at 4° C. Centrifugation is carried out at 20,000 g for 20 minutes on a Centrikon model H-401B centrifuge throughout the purification procedure.

Preparation of cell-free extracts 2 kg of *C. beticola*—infected sugar beet leaves are homogenized in 4 liters of Na-citrate buffer pH 5.0 containing 1 mM DTT, 1 mM Benzamidine (starting buffer) and 200 g Dowex 1×2 (100 um mesh size). The homogenate is squeezed through a double layer of 31 um mesh nylon gauze before centrifugation.

Precipitation with heat and ammonium sulphate

The supernatant fraction obtained after centrifugation is heated at 50° C. for 20 minutes and after cooling to 4° C., the precipitate is collected by centrifugation and removed. Solid ammonium sulphate is added to the supernatant until a 90% saturation is achieved. After centrifugation, the precipitated proteins are dissolved in starting buffer; 1 ml of buffer to 10 g of starting material.

AX1, AX2, and AX3 are purified from the ammonium sulphate precipitated protein fraction. After solubilization the protein solution is dialyzed against 10 mM Tris pH 8.0 containing 1 mM DTT and 1 mM Benzamidine. Denatured proteins are removed by centrifugation and the supernatant is loaded onto a Fast Flow 50 ml Sepharose Q column and a chitin column (prepared as described in WO92/17591), the columns being connected in series. The columns are equilibrated with the Tris buffer prior to loading.

Unbound proteins are removed by extensive washing with the Tris buffer. The unbound protein fraction (200 ml per kg of leaf material extracted) is supplemented to contain buffer H: 1M ammonium sulphate, 10% (v/v) glycerol, 1 mM DTT, 0.1M $K.H_2PO_4$ (pH 7.5). The protein solution is incubated with 50 ml of Phenyl Sepharose (Pharmacia) in buffer H for 2 hours at room temperature. The slurry is loaded on top of a column packed with additional 50 ml of Phenyl Sepharose equilibrated in buffer H. The flow through from the column is found to contain anti-fungal activity whereas the proteins eluted from the column with buffer H without ammonium sulphate do not. All of the purification procedures are carried out at 4° C. except for the Phenyl Sepharose steps.

The flow-through from the Phenyl Sepharose column (400 ml) is dialyzed extensively against 20 mM sodium acetate, 1 mM DTT (pH 5.0) and subsequently loaded onto a column of CM-CL6B Sepharose (Pharmacia). This column is washed with buffer I: 50 mM sodium acetate, 10% (v/v) glycerol, 1 mM DTT (pH 5.0) and finally eluted with 0.25M NaCl in buffer I. The fractions containing protein are pooled and half of the pooled fraction is subjected to gel filtration chromatography on a G-75 Sephadex column (Pharmacia; 2.5×70 cm) equilibrated in 50 mM MES (pH 6.0). Fractions of ten ml are collected. Fractions 26–30 exhibited high anti-fungal activity and are supplemented to contain 5% (w/v) betaine.

Fractions 26–30 from the G-75 Sephadex column are subjected to ion exchange FPLC on a Mono S cationic exchange column (H/R 5/5; Pharmacia) equilibrated in buffer A: 50 mM MES at pH 6.0 containing 5% (w/v) betaine. The bound proteins are eluted with a gradient of 0–0.3M NaCl in 15 ml buffer A. Three major protein peaks are eluted, all containing anti-fungal activity (FIG. 1). Said peaks are successively designated AX1, AX2 and AX3.

Purification of WIN proteins from barley

WIN protein (WIN N) was purified from barley grain or stressed barley leaf as described by Kragh et al. (Plant Sci.

71, 65–68 (1990) or Hejgaard et al. (Febs Letters, 307, 389–392 (1992)).

Figure 2:
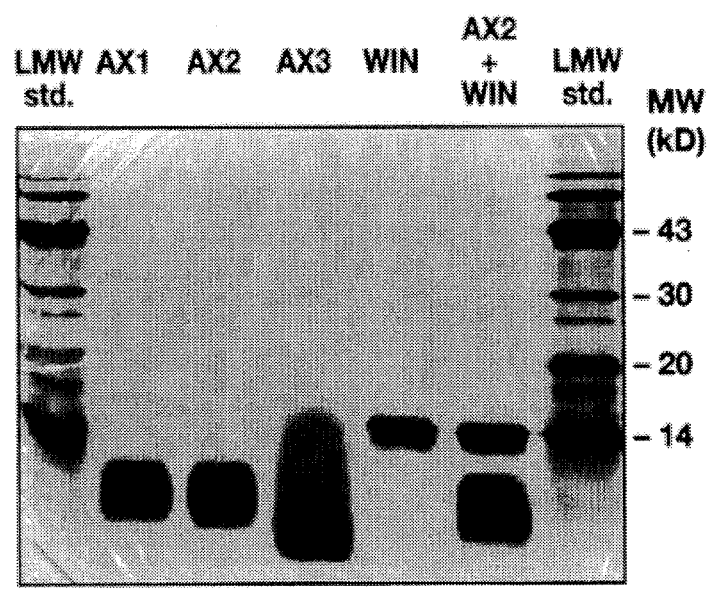
FIG. 2 shows a silver stained polyacrylamide gel of purified AX1, AX2, AX3 and WIN proteins electrophoresed in the presence of SDS and the reducing agent dithiothreitol (DTT): low molecular weight marker proteins are shown in the extreme right and extreme left hand lanes of the gel. The WIN protein is isolated from barley grain.

FIG. 2 shows a silver-stained SDS polyacrylamide gel of the WIN-N protein isolated from barley grain, together with the AX 1, AX2 and AX3 proteins eluted from the Mono S column. Each of the AX proteins is eluted as a fraction which yielded a single band (even if slightly smeared in the case of AX3) under electrophoresis.

AX protein sequencing

Each of the AX proteins is carboxy-methylated and subjected to reverse phase HPLC on a Progel TSK Octadecyl-4PW column (Supelco Inc; 150×4.6 mm). The solvent system is A: 0.1% TFA in water and B: 0.1% TFA in acetonitrile. AX1 and AX2 elute as single symmetrical peaks, and AX3 elutes as two peaks, a major peak followed closely by a minor peak, indicating that there are two forms designated AX3.1 and AX3.2. The AX 1, AX2 and AX3.1 proteins are then sequenced according to standard methods known to those skilled in the art.

Anti-microbial activity of AX1-AX3

Inhibition of fungal growth is measured in 96 well microtitre plates at 620 nm, essentially as described in WO 92/17591.

Proteins AX1, AX2 and AX3, either alone or in combination with WIN N (which is purified from barley grain or stressed barley leaf as described by Hejgaard et al (FEBS Letters, 307, 389–392 (1992)), are incubated with spores of *C. beticola*. The assay mix (240 ul) contains 100 ul of potato dextrose broth (Difco), 60 ul protein sample (or buffer control) in 100 mM Tris and 20 mM NaCl (pH 8.0) as well as approximately 400 spores in 100 ul water. The micro-titre plates are sealed with tape to avoid evaporation and contamination and subsequently incubated at room temperature on an agitator operated at 200 rpm. As is shown in FIG. 3B, the absorbance at 620 nm is measured each day for 8 days and plotted for each concentration of protein vs time. The concentration (ug protein/ml of final assay mix) resulting in 50% inhibition of growth after 72 hours is determined and is termed $I_{50}$.

Figure 3A:
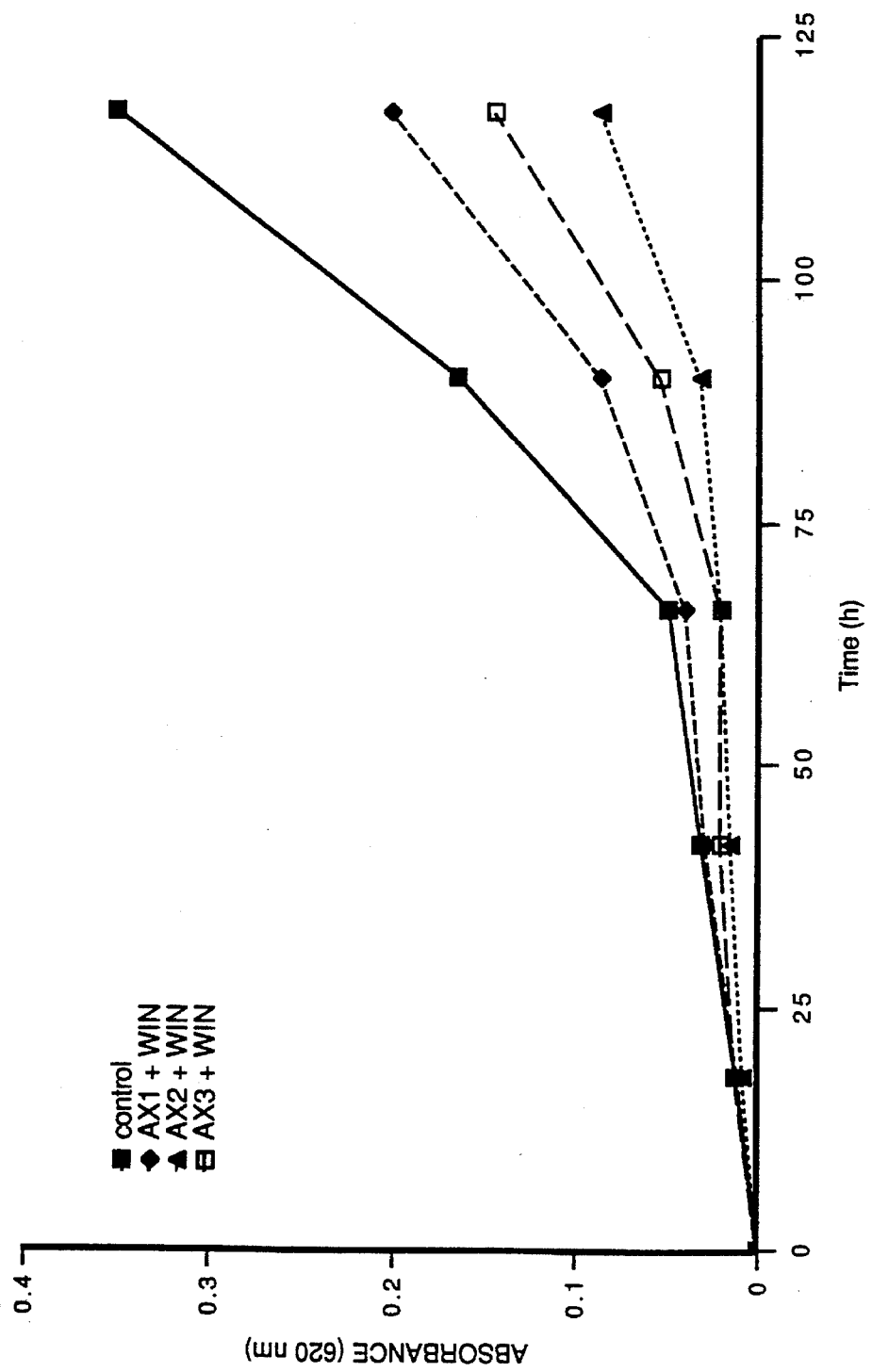
FIGS. 3A and 3B show the anti-fungal activity of AX1, AX3 and AX2, each optionally combined with the WIN protein isolated from barley grain.
Figure 3B:
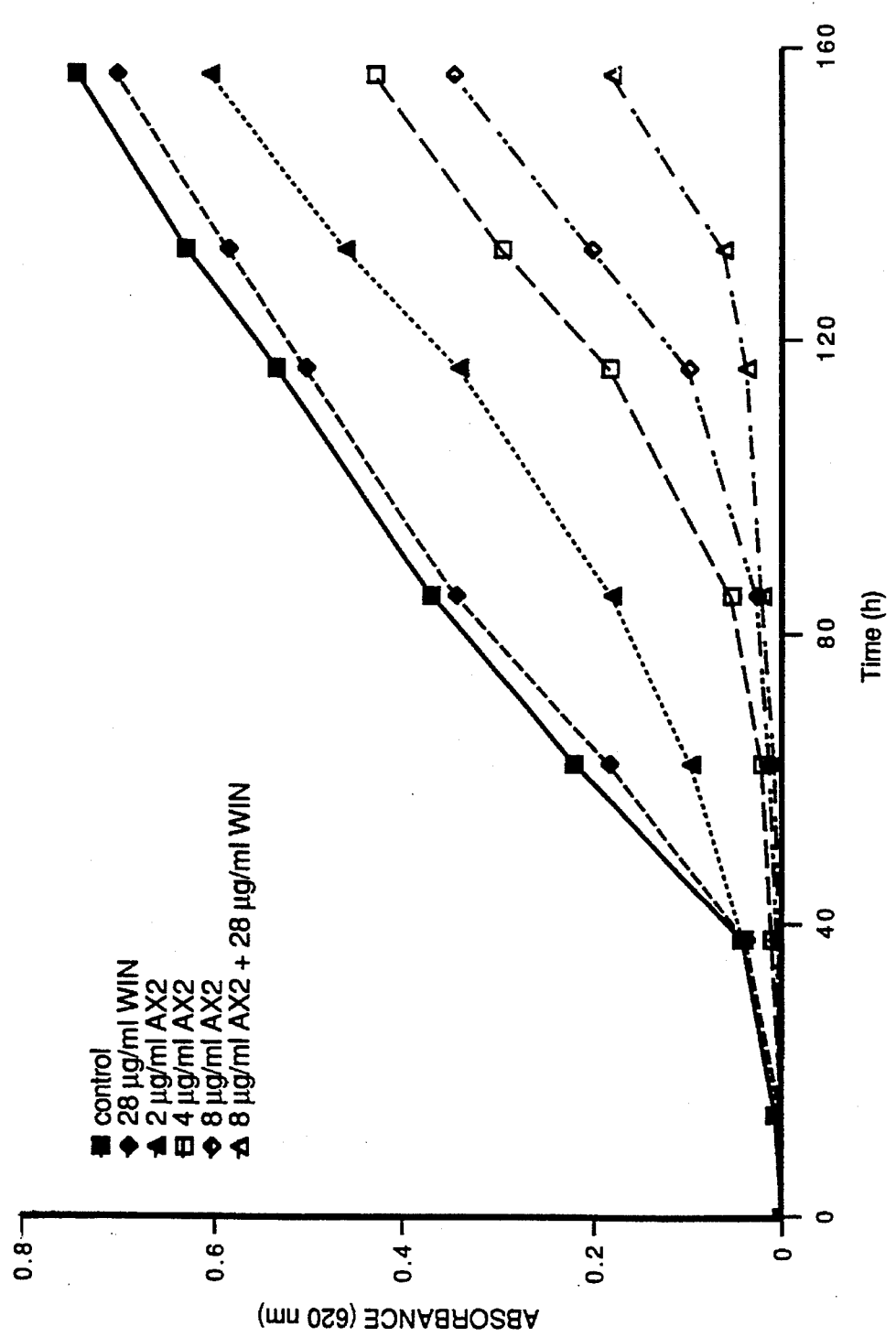
Figure 4A:
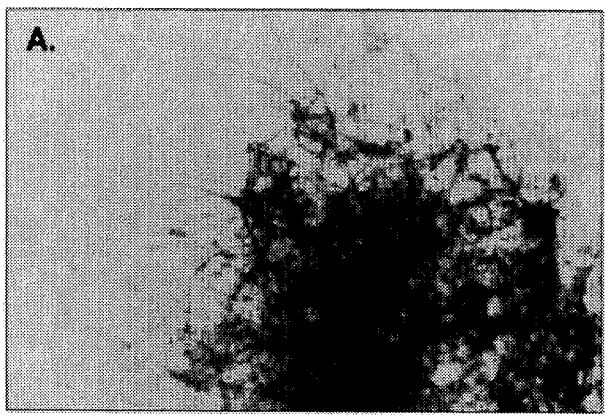
FIGS. 4A–4D show the morphology of *C. beticola* resulting from its treatment with the WIN protein at 28 ug/ml (FIG. B); the AX2 protein at 8 ug/ml (FIG. C); and the combination of AX2 at 8 ug/ml and WIN at 28 ug/ml (FIG. D).
Figure 4B:
Figure 4C:
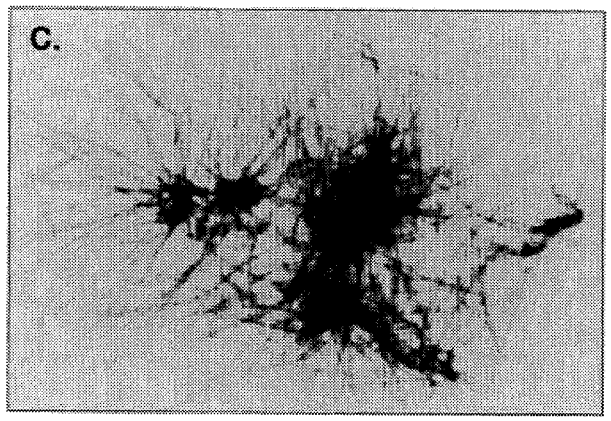
Figure 4D:
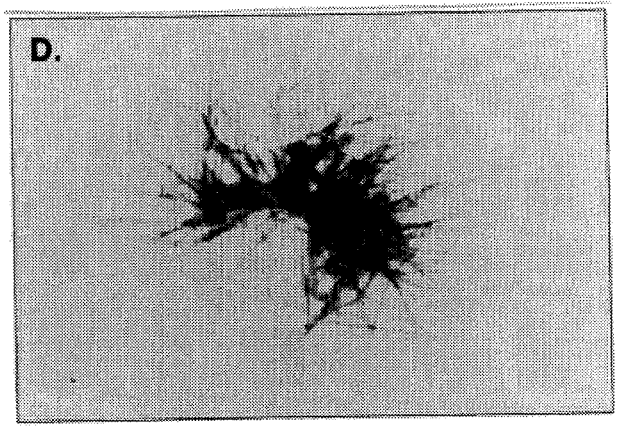

As can be seen from FIGS. 3A and 3B, each of the AX proteins significantly reduces the growth in vitro of *C. beticola*. The anti-fungal activity of AX2 is particularly pronounced, 2 ug/ml (about 0.5 uM) being sufficient for 50% growth inhibition ($I_{50}$) after 72 hours incubation. WIN N alone exhibits a moderate anti-fungal activity with 160 ug/ml (about 11 uM) being required for 50% inhibition of *C. beticola* after 72 hours (data not shown). The combination of AX2 and WIN N produces a significantly enhanced and prolonged growth reduction of the fungus. As is clear from FIG. 3A, the growth inhibitory potential of AX2 against *C. beticola* is greater than that of AX 1.

AX2 and WIN N do not appear to exhibit fungicidal activity against *C. beticola*, but rather profoundly slow the rate of fungal hyphal extension when compared to controls. The morphology of the fungus is also markedly changed as a consequence of treatment with AX2 and/or WIN N (see FIG. 4).

Furthermore, AX1, AX2 and AX3 (and mixtures thereof), optionally in the presence of WIN N, show little, if any, significant detrimental effect on the germination of sugar beet pollen when applied in concentrations which are effective against *C. beticola*, indicating their lack of toxicity against plant cells.

Anti-fungal activity of the AX-proteins against corn pathogens

The AX proteins according to the present invention are assessed for their anti-fungal activity against a number of corn pathogens. Concerning the results depicted in Tables 1 and 2, the assay of the AX proteins in respect of the corn pathogens is performed as follows. Five µl of a solution containing the proteins at the indicated concentrations are aseptically transferred into a well of a sterile, round-bottomed microtiter plate. All treatments are replicated once. Un-inoculated and inoculated culture media minus test protein solution are routinely included as controls. Spores (100–150) are aseptically added to each sample in a 5.0 µl aliquot of double strength Potato Dextrose Broth (PDB).

Following gentle agitation to mix the protein sample and spore suspension, a double layer of parafilm is wrapped around the lid/plate junction in order to minimize desiccation and the thus wrapped microtiter plate is incubated at 19±0.2° C. with a 16 h photoperiod.

Individual wells are scored for spore germination and mycelial growth every 24 h. At the end of 120 h the level of anti-fungal activity is determined. Results are presented in Tables 1 and 2. Table 1 indicates the minimum concentration of protein required to exhibit a growth inhibitory effect on the fungi and Table 2 indicates the concentration of protein which provides a 50% inhibition of growth in comparison with control cultures in which the fungi are grown in the absence of the test proteins.

TABLE 1

| Pathogen/Disease | Minimum inhibitory concentration (µg/ml) | | |
|---|---|---|---|
| | WIN N | AX1 | AX2 |
| *Bioplaris maydis* Southern Corn Leaf Blight | ni | 20 | 30 |
| *Cercospora zeae maydis* Gray Leaf Spot | | | |
| *Colletotrichum graminicola* Anthracnose Stalk Rot | ni | 50 | 50 |
| *Diplodia maydis* Diplodia Ear & Stalk Rot | 64 | 11 | ni |
| *Exserohilum turcicum* race 1 Northern Corn Leaf Blight Race 1 | ni | 11 | 98 |
| *Exserohilum turcicum* race 2 Northern Corn Leaf Blight Race 2 | 193 | 33 | ni |
| *Fusarium graminearum* Fusarium Ear & Stalk Rot | ni | 33 | 33 |
| *Fusarium moniliforme* Fusarium Ear & Stalk Rot | ni | ni | ni |
| *Gibberella zeae* Gibberella Ear & Stalk Rot | ni | ni | ni |

Table 1. Antifungal activity of AX1, AX2 and WIN N against selected corn pathogens. ("ni" indicates that the proteins did not inhibit fungal growth).

Concerning the results shown in Table 3, the assay of the AX and WIN N proteins in respect of the disclosed pathogens is performed as follows. Mycelium from the disclosed fungi are dispersed in a drop of molten agar which is then solidified. The solid agar droplets comprising the encapsulated mycelia are then coated with the test protein in the specified amount. Following incubation for 5 days under moist conditions the amount of mycelial growth is determined in comparison with controls, in which the agar droplets comprising the fungal mycelia are not coated with test protein. The results presented in Table 3 indicate the mount of protein required to produce a 50% inhibition in growth of the fungal pathogens.

TABLE 2

| Pathogen/Disease | AX1 | AX2 | WIN N |
|---|---|---|---|
| | (Protein concentration (μg/ml) providing more than 50% growth inhibition) | | |
| *Colletotrichum graminicola* Anthracnose stalk rot | 50 | 50 | ni[1] |
| *Fusarium moniliforme* | ni | ni | ni |
| *F. graminearum* Fusarium ear and stalk rot | 33 | 33 | ni |
| *Gibberella zeae* Gibberella stalk rot | ni | ni | ni |
| *Diplodia maydis* Diplodia stalk rot | 11 | ni | 64 |
| *Bipolaris maydis* Southern corn leaf blight | 20 | 33 | ni |
| *Exserohilum turcicum* Nothern corn leaf blight | 33 | ni | 193 |

Table 2. Amount of protein required to produce a 50% growth inhibition of the fungal pathogens depicted in Table 1. ("ni" indicates that the proteins did not inhibit fungal growth).

TABLE 3

| | Protein concentration (μg/ml) | | | | |
|---|---|---|---|---|---|
| | AX1 | AX2 | | WIN N | |
| Pathogen/Disease | 20 | 20 | 40 | 20 | 40 |
| | Growth inhibition (%) | | | | |
| *Monilinia fructigena* Brown rot of fruit | 80 | 80 | | ni | |
| *Cochliobolus sativus* Cereal foot rot Cereal eye spot | 30 | 30 | | ni | |
| *Pseudocercosporella herpotrichoides* | 30 | 30 | | | 30 |
| *Pyricularia oryzae* | ni | 20 | | ni | |
| *Rhizoctonia solani* | ni | | 10 | ni | |
| *Fusarium culmorum* | ni | | 10 | ni | |
| *Leptosphaeria nodorum* | ni | | 10 | ni | |
| *Botrytis cinerea* | ni | | 10 | ni | |

Table 3. The percentage inhibition of fungal growth for a specified protein concentration in respect of further pathogens. ("ni" indicates that, at the concentrations tested, the proteins did not inhibit fungal growth).

As is clear from FIGS. 3A, 3B, and 4A–D, together with Tables 1–3, the AX1, AX2 and AX3 proteins, optionally combined with WIN N are fungiostatic. They consequently are able to provide plants, particularly sugar beet and corn, with greatly improved resistance against disease (particularly fungal infections) including that caused by *C. beticola* and numerous corn pathogens.

Protein Sequences

SEQ ID Nos 2, 5 and 8 show the amino acid sequences of the AX proteins 1, 2 and 3.1 respectively. These sequences include the respective signal peptides. In the case of AX1 and AX2, the signal peptides consist of residues 1–28 and the mature proteins consist of residues 29–74. In the case of AX3.1, the putative preprotein includes the mature AX3.1 protein in residues 80–111. SEQ ID No. 11 shows the amino acid sequence of the Barley WIN protein together with its signal peptide.

From their amino acid-sequences it is clear that both AX1 and AX2 are related proteins comprising 46 amino acids each.

From SEQ ID No. 2, the sequence of the AX1 protein absent its signal peptide is:

Ala Ile Cys Lys Lys Pro Ser Lys Phe Phe Lys Gly Ala Cys
Gly Arg Asp Ala Asp Cys Glu Lys Ala Cys Asp Gln Glu
Asn Trp Pro Gly Gly Val Cys Val Pro Phe Leu Arg Cys
Glu Cys Gln Arg Ser Cys

From SEQ ID No. 5, the sequence of the AX2 protein absent its signal peptide is:

Ala Thr Cys Arg Lys Pro Ser Met Tyr Phe Ser Gly Ala Cys
Phe Ser Asp Thr Asn Cys Gln Lys Ala Cys Asn Arg Glu
Asp Trp Pro Asn Gly Lys Cys Leu Val Gly Phe Lys Cys
Glu Cys Gln Arg Pro Cys

From SEQ ID No. 8, the sequence of the AX3.1 protein absent its signal peptide is:

Arg Cys Ile Pro Cys Gly Gln Asp Cys Ile Ser Ser Arg Asn
Cys Cys Ser Pro Cys Lys Cys Asn Phe Gly Pro Pro Val
Pro Arg Cys Thr Asn

The first 45 residues from the N-terminal of each protein are obtained by amino acid sequencing. The 461 h residue of both AX1 and AX2 are identified as cysteine, on the basis of the nucleotide sequences of the respective cDNAs (SEQ ID Nos 1 and 4 respectively) obtained by PCR, taken together with homology with related proteins from other plants. AX3.1, which is a basic protein, comprises 32 amino acids, the sequence of which is in agreement with its cDNA as obtained by PCR (see SEQ ID No 7).

Moreover, the amino acid sequence data of the AX proteins was substantiated by an analysis of the amino acid compositions of the respective proteins (see Table 4), as well as by mass spectrometry of the pure proteins compared with their molecular weights deduced from the genes encoding them (see Table 5). Curiously, AX2 (probably a methionine residue therein) appears, from the mass spectrometry analysis, to be oxidized. Such oxidation may artefactually result from the said mass analysis.

Figure 5A:
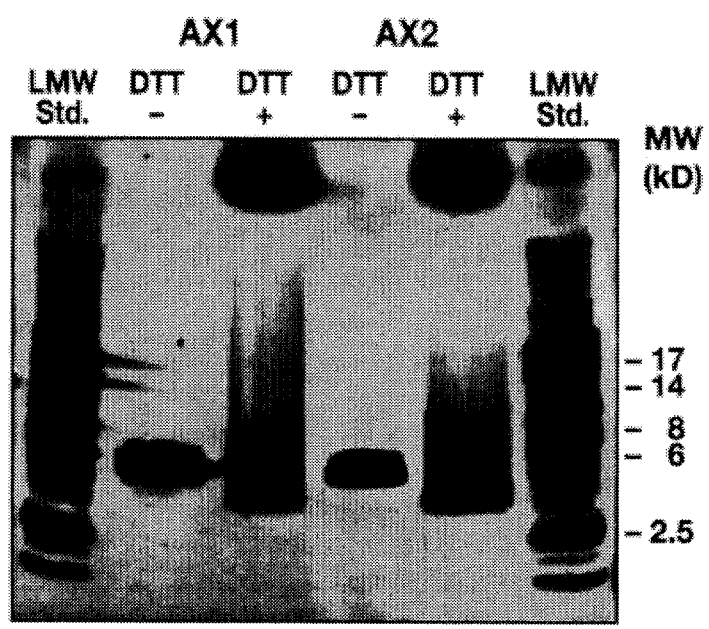
FIG. 5 shows a silver stained polyacrylamide gel of purified AX1, AX2 and AX3 proteins electrophoresed in the presence of SDS and in the presence or absence of the reducing agent dithiothreitol (DTT). In contrast to AX1 and AX2, the electrophoretic mobility of the two isoforms of AX3, AX3.1 and AX3.2, is strongly influenced by the presence of DTT indicating that AX3.1 and AX3.2 probably exist as dimers if not trimers. The relatively high background staining in the gel which manifests itself in the vicinity of the protein bands as an apparent smearing is due to artifactual oxidation of the protein during electrophoresis, whereas the background staining at the top of the gels is due to artifactual staining of DTT. The slight shift in apparent molecular weight for the AX1 and AX2 proteins in the presence of DTT is probably due to unfolding caused by disruption of intramolecular disulfide bridges leading to enhanced binding of SDS in comparison with the same proteins denatured by SDS in the absence of DTT. As in FIG. 2, low molecular weight marker proteins (designated as LMW in the Figure) are included in the gels.
Figure 5B:
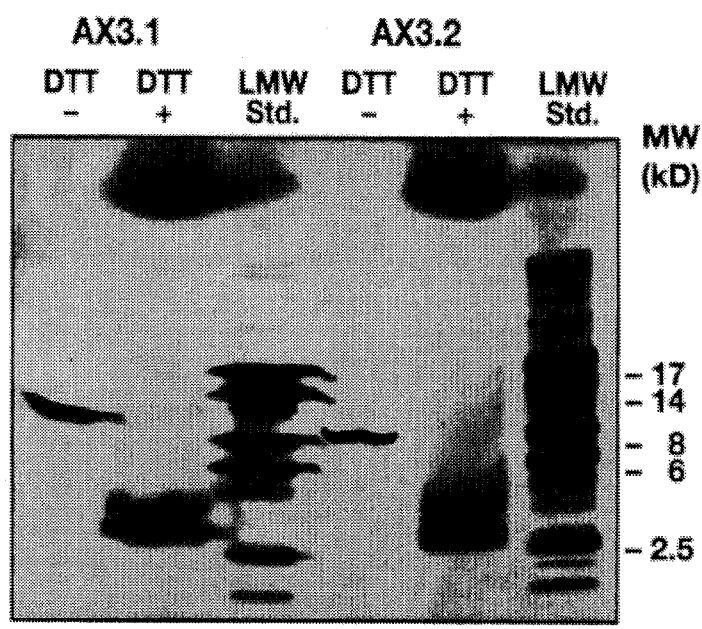

AX1 and AX2 exhibit some sequence similarity (about 54%) to gamma-thionins from wheat and barley, putative inhibitors from sorghum of insect alpha amylase, and antifungal proteins isolated from radish seeds. The radish proteins are known to be potent anti-fungal proteins and are suggested to inhibit fungal growth by interfering with calcium ion signalling. AX1 anti AX2, however, exhibit little sequence similarity (less than 45%) with such radish proteins. Moreover, such radish proteins are active predominantly in oligomeric form (trimers or tetramers), whereas gel-filtration and SDS electrophoresis in the absence of DTT or mercaptoethanol indicate that AX 1 and AX2 are monomeric (see FIG. 5 for example). No substantial sequence homology exists between AX3 and other proteins.

TABLE 4

Amino acid composition of the AX Proteins

| Residue | AX1 | AX2 | AX3 |
|---|---|---|---|
| Asp | 4.0 | 5.0 | 4.1 |
| Thr | 0.1 | 2.0 | 1.0 |
| Ser | 2.1 | 3.1 | 3.0 |
| Glx | 5.7 | 4.4 | 1.1 |
| Pro | 3.2 | 3.2 | 5.1 |
| Gly | 4.3 | 3.2 | 2.1 |
| Ala | 4.1 | 3.1 | 0.0 |
| Cys | 6.9 | 6.9 | 6.2 |
| Val | 2.0 | 1.1 | 1.0 |
| Met | 0.0 | 0.9 | 0.0 |
| Ile | 1.0 | 0.1 | 2.0 |
| Leu | 1.1 | 1.1 | 0.0 |
| Tyr | 0.0 | 0.9 | 0.0 |
| Phe | 3.1 | 3.0 | 1.0 |
| His | 0.0 | 0.0 | 0.0 |
| Lys | 5.1 | 4.0 | 1.0 |
| Arg | 3.2 | 3.1 | 3.2 |
| Trp | n.d. | n.d. | n.d. |

TABLE 5

Molecular weights of AX1, 2 and 3.1 determined by
Electro-Spray Mass spectrometry (ES-MS) and
deduced from the genes encoding them.

| Protein | Molecular Weight (Da) | |
|---|---|---|
| | ES-MS | Derived from cDNA (−8H$^+$) |
| AX1 | 5078.1 | 5086 − 8 = 5078 |
| AX2 | 5193.4 | 5185 − 8 + 16 = 5193 |
| AX3.1 | 3452.5 | 3460 − 8 = 3452 |

Production of transformed plants

The genes encoding the AX proteins are introduced into plants. Based on gene specific primers, the coding regions of the genes encoding AX1, AX2 and AX3.1 are synthesized from corresponding mRNA using PCR, namely 3' RACE followed by 5' RACE. After addition of a suitable promoter (such as 35S) and terminator (such as 35S) sequence, the genes encoding the AX proteins are introduced into a plant transformation vector. It is preferred that a translation enhancing sequence is introduced into the vector at a site 5' of the protein coding region (see SEQ ID Nos 3, 6 and 9 for example). The vector also contains suitable marker genes of the kind known to the skilled man. The vector optionally includes a gene encoding a WIN protein, such as that obtained from stressed barley leaf or barley grain (together with a translation enhancing sequence if desirable, see SEQ ID No. 13, for example), and/or a gene encoding a chitinase and/or a glucanase. The preferred chitinase if the chitinase 4 described in PCT Patent Application No. PCT/DK92/00108 (Publication No. WO92/17591). *Agrobacterium tumefaciens*, for example, may be transformed with these vectors. Plant cells are then treated with such transformed Agrobacterium, and the thus transformed plant cells are regenerated into whole plants, in which the new nuclear material is stably incorporated into the genome. It will be appreciated, however, that the DNA encoding an AX protein (or combination of such proteins), optionally further encoding a WIN protein and/or a chitinase and/or a glucanase (or combination of such proteins), may be introduced into plant cells by other known methods, including use of a micro-projectile gun, electroporation, electro-transformation, and micro-injection etc, and that regeneration of transformed plant cells is carried out according to methods known to the skilled man, including treatment of the cells with cytokinins where this is necessary or desirable in order to improve the regeneration frequency.

Potatoes and sugar beet transgenic for the AX proteins are thus produced. Recombinant DNA sequences comprising, for example, a sequence selected from SEQ ID Nos 3, 6 or 9 are introduced by known means (including co-transformation) into potato or sugar beet. It will be appreciated that recombinant DNA comprising the sequences depicted in SEQ ID Nos. 1, 4 or 7 could alternatively be used, although they lack an introduced translation enhancing element 5' to the start codon of the coding region of the various AX protein signal peptides. Expression of the gene encoding AX2, for example, is detected by identifying the AX2 gene transcription product. The presence of the protein in the plant is further demonstrated immunochemically using antibodies raised against an authentic sample of the protein. In order to increase the immunogenicity of the proteins they may be linked to diphtheria toxoid carrier or coupled to poly-lysine prior to injection into rabbits.

Extracts of transgenic potato and sugar beet are produced, partially purified, and assayed, according to the micro-titre assay described above, for their ability to inhibit the growth of Cercospora.

Extracts obtained from plants transgenic for the AX protein substantially inhibit the growth of the fungus in comparison with like extracts obtained from non-transgenic control potatoes or sugar beet.

Moreover, suitable micro-organisms (i.e. those in which the production of AX proteins is not substantially toxic) may be transformed with a vector comprising the gene (or genes) encoding an AX protein (or combination of AX proteins) so that the transformed micro-organisms produce such protein. The micro-organisms may further comprise the gene encoding other proteins, such as a WIN protein of the kind disclosed in SEQ ID No. 11 and/or various chitinases and/or glucanases. A particularly preferred such other protein is the chitinase 4 as described in PCT Patent Application No. PCT/DK92/00108 (Publication No. WO92/17591).

These micro-organisms may then be used to combat plant pathogens. For example, the transformed micro-organisms may be dried and sprayed onto infected plants or plants at risk of infection.

We claim:
1. Isolated DNA comprising a sequence encoding a protein selected from the group of those depicted in SEQ ID Nos. 2, 5 and 8.
2. Isolated DNA according to claim 1 wherein the protein is capable of exerting an anti-microbial effect against *Bioplaris maydis, Cercospora beticola, Cercospora zea maydis, Colletotrichum graminicola, Diplodia maydis, Exserohilum turcicum* race 1 and 2, *Fusarium graminearum, Monilinia fructigena, Cochliobolus sativus, Pseudocercosporella herpotrichoides, Pyrocularia oryze, Rhizoctonia solani, Fusarium culmorum, Leptosphaeria nodorum* or *Botrytis cinema*.
3. Isolated DNA according to claim 1 wherein the protein includes residues 80-111 of SEQ ID No. 8, residues 29-74 of SEQ ID No. 2 or residues 29-74 of SEQ ID No. 5 or mixtures thereof.
4. Isolated DNA according to claim 2 wherein the protein includes residues 80-111 of SEQ ID No. 8.
5. Isolated DNA according to claim 2 wherein the protein includes residues of 29-74 of SEQ ID No. 2.
6. Isolated DNA according to claim 2 wherein the protein includes residues 29-74 of SEQ ID No. 5.
7. Isolated DNA according to claim 1 further comprising a sequence encoding a chitin-binding WIN protein.
8. Isolated DNA according to claim 7 wherein said WIN encoding sequence encodes a protein depicted in SEQ ID No. 11.
9. Isolated DNA according to claim 1 which further comprises a DNA sequence encoding a protein which is the basic counter-part of the acidic pathogenesis related 4 group of proteins.
10. Isolated DNA according to claim 1 further comprising a DNA sequence encoding a chitinase protein.
11. Isolated DNA according to claim 1 further comprising a DNA sequence encoding a glucanase protein.
12. Isolated DNA comprising a sequence selected from the group consisting of SEQ ID No. 1,3, 4, 6, 7 and 9.
13. Isolated DNA according to claim 1 which is modified in that codons which are preferred by the organism into which the recombinant DNA is to be inserted are used so that expression of the modified DNA in said organism yields the same protein as that obtained by expression of the unmodified recombinant DNA in the organism in which the protein-encoding components of the recombinant DNA are endogenous.

14. A DNA sequence which hybridizes under stringent conditions with the DNA sequence of claim 1 and which encodes a protein that is capable of exerting the same antimicrobial effect as a protein selected from the group consisting of SEQ ID NOs: 2, 5 and 8.

15. Microorganisms transformed with the DNA sequence according to claim 1.

16. Plants transformed with the DNA sequence according to claim 1.

17. The transformed plants of claim 16 wherein said plants are corn plants.

18. The transformed plants of claim 16 wherein said plants are sugarbeet plants.

19. The progeny and seeds of the transformed plants of claim 10 wherein the progeny express said recombinant DNA.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 437 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Beta vulgaris ( i x ) FEATURE:

(A) NAME/KEY: CDS
(B) LOCATION: 40..264

(xi) SEQUENCE DESCRIPTION: SEQ ID NO:1:

```
ATACGCATTT GTTTCAAAGT TCAAACAAAG ACCAAAAAA ATG GAG AAG AAA TTC           54
                                            Met Glu Lys Lys Phe
                                             1                 5

TTT GGG CTT TTG CTT TTG CTA CTC TTC GTA TTT GCT TCT GAG ATG AAT         102
Phe Gly Leu Leu Leu Leu Leu Leu Phe Val Phe Ala Ser Glu Met Asn
                10                  15                  20

ATT GTG ACT AAG GTT GAT GGT GCA ATA TGC AAG AAA CCA AGT AAG TTC         150
Ile Val Thr Lys Val Asp Gly Ala Ile Cys Lys Lys Pro Ser Lys Phe
             25                  30                  35

TTC AAA GGT GCT TGC GGT AGA GAT GCC GAT TGT GAG AAG GCT TGT GAT         198
Phe Lys Gly Ala Cys Gly Arg Asp Ala Asp Cys Glu Lys Ala Cys Asp
         40                  45                  50

CAA GAG AAT TGG CCT GGC GGA GTT TGT GTA CCC TTT CTC AGA TGT GAA         246
Gln Glu Asn Trp Pro Gly Gly Val Cys Val Pro Phe Leu Arg Cys Glu
     55                  60                  65

TGT CAG AGG TCT TGC TAAGCACTGC AAGCCACGGA CGATAAAAG AAGTACTTGT          301
Cys Gln Arg Ser Cys
 70              75

AATGAAGCTA TGGGTCAATA TTTTTCAATC CTATAATATT AAATAAATTG TTGTAACTAT       361

TTTAAGTGTG TAATAAATCT ACGTGGGTTT AAACTCCACA ATTGCTTTTG AAATAATGAT       421

TTACATATAA GTTTCA                                                      437
```

(2) INFORMATION FOR SEQ ID NO:2:

(i) SEQUENCE CHARACTERISTICS:
   (A) LENGTH: 74 amino acids
   (B) TYPE: amino acid
   (D) TOPOLOGY: linear (ii) MOLECULE TYPE: protein (xi) SEQUENCE DESCRIPTION: SEQ ID NO:2:

```
Met Glu Lys Lys Phe Phe Gly Leu Leu Leu Leu Leu Phe Val Phe
 1               5                  10                  15

Ala Ser Glu Met Asn Ile Val Thr Lys Val Asp Gly Ala Ile Cys Lys
                 20                  25                  30

Lys Pro Ser Lys Phe Phe Lys Gly Ala Cys Gly Arg Asp Ala Asp Cys
             35                  40                  45

Glu Lys Ala Cys Asp Gln Glu Asn Trp Pro Gly Gly Val Cys Val Pro
     50                  55                  60

Phe Leu Arg Cys Glu Cys Gln Arg Ser Cys
 65                  70
```

(2) INFORMATION FOR SEQ ID NO:3:

(i) SEQUENCE CHARACTERISTICS:
   (A) LENGTH: 349 base pairs
   (B) TYPE: nucleic acid
   (C) STRANDEDNESS: double
   (D) TOPOLOGY: unknown (ii) MOLECULE TYPE: cDNA (iii) HYPOTHETICAL: NO (iii) ANTI-SENSE: NO (vi) ORIGINAL SOURCE:
   (A) ORGANISM: Beta vulgaris ( x i ) SEQUENCE DESCRIPTION: SEQ ID NO:3:

| | | | | | |
|---|---|---|---|---|---|
| CTGCAGGGAT | CCTATTTTTA | CAACAATTAC | CAACAACAAC | AAACAACAAA | CAACATTACA | 60 |
| ATTACTATTT | ACAATTACAC | CATGGAGAAG | AAATTCTTTG | GGCTTTTGCT | TTTGCTACTC | 120 |
| TTCGTATTTG | CTTCTGAGAT | GAATATTGTG | ACTAAGGTTG | ATGGTGCAAT | ATGCAAGAAA | 180 |
| CCAAGTAAGT | TCTTCAAAGG | TGCTTGCGGT | AGAGATGCCG | ATTGTGAGAA | GGCTTGTGAT | 240 |
| CAAGAGAATT | GGCCTGGCGG | AGTTTGTGTA | CCCTTTCTCA | GATGTGAATG | TCAGAGGTCT | 300 |
| TGCTAAGCAC | TGCAAGCCAC | GGACGATAAA | AAGAAGCGTC | GACGCATGC | | 349 |

( 2 ) INFORMATION FOR SEQ ID NO:4:

( i ) SEQUENCE CHARACTERISTICS:
        ( A ) LENGTH: 492 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Beta vulgaris ( i x ) FEATURE:
        ( A ) NAME/KEY: CDS
        ( B ) LOCATION: 53..277

( x i ) SEQUENCE DESCRIPTION: SEQ ID NO:4:

```
CCATACATTA TATACGTATT TGTTTCAAAG TTCAAACAAA GACAAAACAA AA ATG                55
                                                          Met
                                                           1

GAG AAA AAA TTC TTT GGG CTT TTG CTT TTG CTA CTC TTC GTA TTT GCT            103
Glu Lys Lys Phe Phe Gly Leu Leu Leu Leu Leu Leu Phe Val Phe Ala
              5                   10                  15

TCT GAG CTG AAC ATG GTG GCT GAG GTT CAA GGT GCC ACT TGT AGA AAA            151
Ser Glu Leu Asn Met Val Ala Glu Val Gln Gly Ala Thr Cys Arg Lys
         20                  25                  30

CCA AGT ATG TAT TTC AGC GGC GCT TGC TTT TCT GAT ACG AAT TGT CAG            199
Pro Ser Met Tyr Phe Ser Gly Ala Cys Phe Ser Asp Thr Asn Cys Gln
     35                  40                  45

AAA GCT TGT AAT CGA GAG GAT TGG CCT AAT GGG AAA TGC TTA GTC GGT            247
Lys Ala Cys Asn Arg Glu Asp Trp Pro Asn Gly Lys Cys Leu Val Gly
 50                  55                  60                  65

TTC AAA TGT GAA TGT CAA AGG CCT TGT TAAGTGGTGC CTGTGTCCTC                  294
Phe Lys Cys Glu Cys Gln Arg Pro Cys
             70                  75
```

| | | | | |
|---|---|---|---|---|
| AATTACGGCC | TACGAGCCTT | TCAGGTACCT | ATGTGGCCGA | GTATGGCTAA ATTGGTAATA | 354 |
| GTACATAGCA | GTGGTAATAT | GAATAAACGA | TTCACTCTTG | TAAGATGTAT TATGTTTTGT | 414 |
| TTGTGCTGTG | GTTCCAGTT | GCTTTTGAAA | ATAATGATTT | TCATATAAAT CGGACCTTTT | 474 |
| ATTCTGATAA | AAAAAAAA | | | | 492 |

( 2 ) INFORMATION FOR SEQ ID NO:5:

( i ) SEQUENCE CHARACTERISTICS:
        ( A ) LENGTH: 74 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Glu | Lys | Lys | Phe | Phe | Gly | Leu | Leu | Leu | Leu | Leu | Leu | Phe | Val | Phe |
|---|---|---|---|---|---|---|---|---|---|---|---|---|---|---|---|
| 1 | | | | 5 | | | | | 10 | | | | | 15 | |

| Ala | Ser | Glu | Leu | Asn | Met | Val | Ala | Glu | Val | Gln | Gly | Ala | Thr | Cys | Arg |
|---|---|---|---|---|---|---|---|---|---|---|---|---|---|---|---|
| | | | 20 | | | | | 25 | | | | | 30 | | |

| Lys | Pro | Ser | Met | Tyr | Phe | Ser | Gly | Ala | Cys | Phe | Ser | Asp | Thr | Asn | Cys |
|---|---|---|---|---|---|---|---|---|---|---|---|---|---|---|---|
| | | 35 | | | | | 40 | | | | | 45 | | | |

| Gln | Lys | Ala | Cys | Asn | Arg | Glu | Asp | Trp | Pro | Asn | Gly | Lys | Cys | Leu | Val |
|---|---|---|---|---|---|---|---|---|---|---|---|---|---|---|---|
| | 50 | | | | | 55 | | | | | 60 | | | | |

| Gly | Phe | Lys | Cys | Glu | Cys | Gln | Arg | Pro | Cys |
|---|---|---|---|---|---|---|---|---|---|
| 65 | | | | 70 | | | | | |

( 2 ) INFORMATION FOR SEQ ID NO:6:

( i ) SEQUENCE CHARACTERISTICS:
        ( A ) LENGTH: 363 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Beta vulgaris ( x i ) SEQUENCE DESCRIPTION: SEQ ID NO:6:

| | | | | | |
|---|---|---|---|---|---|
| CTGCAGGGAT | CCTATTTTTA | CAACAATTAC | CAACAACAAC | AAACAACAAA | CAACATTACA | 60 |
| ATTACTATTT | ACAATTACAC | CATGGAGAAA | AAATTCTTTG | GGCTTTTGCT | TTTGCTACTC | 120 |
| TTCGTATTTG | CTTCTGAGCT | GAACATGGTG | GCTGAGGTTC | AAGGTGCCAC | TTGTAGAAAA | 180 |
| CCAAGTATGT | ATTTCAGCGG | CGCTTGCTTT | TCTGATACGA | ATTGTCAGAA | AGCTTGTAAT | 240 |
| CGAGAGGATT | GGCCTAATGG | GAAATGCTTA | GTCGGTTTCA | AATGTGAATG | TCAAAGGCCT | 300 |
| TGTTAAGTGG | TGCCTGTGTC | CTCAATTACG | GCCTACGAGC | CTTTCAGGTA | CGTCGACGCA | 360 |
| TGC | | | | | | 363 |

( 2 ) INFORMATION FOR SEQ ID NO:7:

( i ) SEQUENCE CHARACTERISTICS:
        ( A ) LENGTH: 596 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Beta vulgaris ( i x ) FEATURE:
        ( A ) NAME/KEY: CDS
        ( B ) LOCATION: 23..358

( x i ) SEQUENCE DESCRIPTION: SEQ ID NO:7:

```
ATTCAACCCA ATAGAAACAA TC ATG GCA AGG AAC TCA TTC AAC TTC CTC ATT        52
                         Met Ala Arg Asn Ser Phe Asn Phe Leu Ile
                          1               5                   10

ATC ATG GTC ATT TCA GCA CTG CTT TTG CTC CCT GGA TCA CGT GCA AGC         100
```

|  |  |  |  |  |  |  |  |  |  |  |  |  |  |  |  |
|---|---|---|---|---|---|---|---|---|---|---|---|---|---|---|---|
| Ile | Met | Val | Ile | Ser<br>15 | Ala | Leu | Leu | Leu | Pro<br>20 | Gly | Ser | Arg | Ala<br>25 | Ser | |

| TTT | CAG | GAA | AAG | ATA | ACT | ATG | AAC | ATA | GAA | GAT | GGA | CGC | GAA | AGC | GGC | 148 |
|---|---|---|---|---|---|---|---|---|---|---|---|---|---|---|---|---|
| Phe | Gln | Glu | Lys<br>30 | Ile | Thr | Met | Asn | Ile<br>35 | Glu | Asp | Gly | Arg | Glu<br>40 | Ser | Gly | |

| ATA | GCA | AAG | GAA | ATA | GTT | GAG | GCA | GAA | GCA | GAA | GCA | GAA | GCA | TTA | TTA | 196 |
|---|---|---|---|---|---|---|---|---|---|---|---|---|---|---|---|---|
| Ile | Ala | Lys<br>45 | Glu | Ile | Val | Glu | Ala<br>50 | Glu | Ala | Glu | Ala | Glu<br>55 | Ala | Leu | Leu | |

| CGC | GTT | GGT | GAG | CAA | GCT | ATG | CTG | GAA | CAA | GTA | ATG | ACA | AGA | GGC | TTA | 244 |
|---|---|---|---|---|---|---|---|---|---|---|---|---|---|---|---|---|
| Arg | Val<br>60 | Gly | Glu | Gln | Ala | Met<br>65 | Leu | Glu | Gln | Val | Met<br>70 | Thr | Arg | Gly | Leu | |

| GCA | GAT | AAC | CTT | AAG | AGG | TGT | ATA | CCA | TGT | GGT | CAA | GAC | TGC | ATT | TCC | 292 |
|---|---|---|---|---|---|---|---|---|---|---|---|---|---|---|---|---|
| Ala | Asp<br>75 | Asn | Leu | Lys | Arg<br>80 | Cys | Ile | Pro | Cys | Gly<br>85 | Gln | Asp | Cys | Ile | Ser<br>90 | |

| TCA | AGA | AAC | TGT | TGC | TCA | CCT | TGC | AAA | TGC | AAC | TTC | GGG | CCA | CCG | GTT | 340 |
|---|---|---|---|---|---|---|---|---|---|---|---|---|---|---|---|---|
| Ser | Arg | Asn | Cys | Cys<br>95 | Ser | Pro | Cys | Lys | Cys<br>100 | Asn | Phe | Gly | Pro | Pro<br>105 | Val | |

| CCA | AGG | TGT | ACT | AAT | TGAATGCTTA | GCTTGCTGCT | TAGTGCTAAA | TGCTAAGCGC | 395 |
|---|---|---|---|---|---|---|---|---|---|
| Pro | Arg | Cys | Thr<br>110 | Asn | | | | | |

| TACGCTTGCT | AGTATGTGCA | CGATCCGCTC | TATCTCTTTA | TATGCACCTA | AGTCCTTTCA | 455 |
|---|---|---|---|---|---|---|

| TCTCGACTGT | GTTGTTTGTG | TGTAAAATAA | AGTCTTGGTT | TTCCAAGACT | ACTAGTTTAG | 515 |
|---|---|---|---|---|---|---|

| TTACTGGCTT | ATGTTTTTCG | GAATCTTGAT | ATATAAATAA | GACAAGGAGA | CCTATTTCTT | 575 |
|---|---|---|---|---|---|---|

| GCTTTGCTTA | AAAAAAAAAA | A | | | | 596 |
|---|---|---|---|---|---|---|

( 2 ) INFORMATION FOR SEQ ID NO:8:

( i ) SEQUENCE CHARACTERISTICS:
        ( A ) LENGTH: 111 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Met<br>1 | Ala | Arg | Asn | Ser<br>5 | Phe | Asn | Phe | Leu | Ile<br>10 | Ile | Met | Val | Ile | Ser<br>15 | Ala |
|---|---|---|---|---|---|---|---|---|---|---|---|---|---|---|---|
| Leu | Leu | Leu | Leu<br>20 | Pro | Gly | Ser | Arg | Ala<br>25 | Ser | Phe | Gln | Glu | Lys<br>30 | Ile | Thr |
| Met | Asn | Ile<br>35 | Glu | Asp | Gly | Arg | Glu<br>40 | Ser | Gly | Ile | Ala | Lys<br>45 | Glu | Ile | Val |
| Glu | Ala<br>50 | Glu | Ala | Glu | Ala | Glu<br>55 | Ala | Leu | Leu | Arg | Val<br>60 | Gly | Glu | Gln | Ala |
| Met<br>65 | Leu | Glu | Gln | Val | Met<br>70 | Thr | Arg | Gly | Leu | Ala<br>75 | Asp | Asn | Leu | Lys | Arg<br>80 |
| Cys | Ile | Pro | Cys | Gly<br>85 | Gln | Asp | Cys | Ile | Ser<br>90 | Ser | Arg | Asn | Cys | Cys<br>95 | Ser |
| Pro | Cys | Lys | Cys<br>100 | Asn | Phe | Gly | Pro | Pro<br>105 | Val | Pro | Arg | Cys | Thr<br>110 | Asn | |

( 2 ) INFORMATION FOR SEQ ID NO:9:

( i ) SEQUENCE CHARACTERISTICS:
        ( A ) LENGTH: 484 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Beta vulgaris ( x i ) SEQUENCE DESCRIPTION: SEQ ID NO:9:

| | | | | | |
|---|---|---|---|---|---|
| CTGCAGGGAT | CCTATTTTTA | CAACAATTAC | CAACAACAAC | AAACAACAAA | CAACATTACA | 60 |
| ATTACTATTT | ACAATTACAC | CATGGCAAGG | AACTCATTCA | ACTTCCTCAT | TATCATGGTC | 120 |
| ATTTCAGCAC | TGCTTTTGCT | CCCTGGATCA | CGTGCAAGCT | TTCAGGAAAA | GATAACTATG | 180 |
| AACATAGAAG | ATGGACGCGA | AAGCGGCATA | GCAAGGAAA | TAGTTGAGGC | AGAAGCAGAA | 240 |
| GCAGAAGCAT | TATTACGCGT | TGGTGAGCAA | GCTATGCTGG | AACAAGTAAT | GACAAGAGGC | 300 |
| TTAGCAGATA | ACCTTAAGAG | GTGTATACCA | TGTGGTCAAG | ACTGCATTTC | CTCAAGAAAC | 360 |
| TGTTGCTCAC | CTTGCAAATG | CAACTTCGGG | CCACCGGTTC | CAAGGTGTAC | TAATTGAATG | 420 |
| CTTAGCTTGC | TGCTTAGTGC | TAAATGCTAA | GCGCTACGCT | TGCTAGTATG | TGGTCGACGC | 480 |
| ATGC | | | | | | 484 |

( 2 ) INFORMATION FOR SEQ ID NO:10:

( i ) SEQUENCE CHARACTERISTICS:
    ( A ) LENGTH: 504 base pairs
    ( B ) TYPE: nucleic acid
    ( C ) STRANDEDNESS: double
    ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Hordeum vulgare ( i x ) FEATURE:
    ( A ) NAME/KEY: CDS
    ( B ) LOCATION: 1..441

( x i ) SEQUENCE DESCRIPTION: SEQ ID NO:10:

| | | | | | | | | | | | | | | | | |
|---|---|---|---|---|---|---|---|---|---|---|---|---|---|---|---|---|
| ATG | GCG | GCA | CGC | CTG | ATG | CTG | GTG | GCG | GCG | CTG | CTG | TGC | GCG | GCG | GCG | 48 |
| Met | Ala | Ala | Arg | Leu | Met | Leu | Val | Ala | Ala | Leu | Leu | Cys | Ala | Ala | Ala | |
| 1 | | | | 5 | | | | | 10 | | | | | 15 | | |
| GCC | ATG | GCC | ACG | GCG | CAG | CAG | GCG | AAC | AAC | GTC | CGG | GCG | ACG | TAC | CAC | 96 |
| Ala | Met | Ala | Thr | Ala | Gln | Gln | Ala | Asn | Asn | Val | Arg | Ala | Thr | Tyr | His | |
| | | | 20 | | | | | 25 | | | | | 30 | | | |
| TAC | TAC | CGG | CCG | GCG | CAG | AAC | AAC | TGG | GAC | CTG | GGC | GCG | CCC | GCC | GTG | 144 |
| Tyr | Tyr | Arg | Pro | Ala | Gln | Asn | Asn | Trp | Asp | Leu | Gly | Ala | Pro | Ala | Val | |
| | | 35 | | | | 40 | | | | | 45 | | | | | |
| AGC | GCC | TAC | TGC | GCG | ACC | TGG | GAC | GCC | AGC | AAG | CCG | CTG | TCG | TGG | CGG | 192 |
| Ser | Ala | Tyr | Cys | Ala | Thr | Trp | Asp | Ala | Ser | Lys | Pro | Leu | Ser | Trp | Arg | |
| | 50 | | | | | 55 | | | | 60 | | | | | | |
| TCC | AAG | TAC | GGC | TGG | ACG | GCG | TTC | TGC | GGC | CCC | GCC | GGC | CCC | CGC | GGG | 240 |
| Ser | Lys | Tyr | Gly | Trp | Thr | Ala | Phe | Cys | Gly | Pro | Ala | Gly | Pro | Arg | Gly | |
| 65 | | | | | 70 | | | | | 75 | | | | | 80 | |
| CAG | GCG | GCC | TGC | GGC | AAG | TGC | CTC | CGG | GTG | ACC | AAC | CCG | GCG | ACG | GGG | 288 |
| Gln | Ala | Ala | Cys | Gly | Lys | Cys | Leu | Arg | Val | Thr | Asn | Pro | Ala | Thr | Gly | |
| | | | | 85 | | | | | 90 | | | | | 95 | | |
| GCG | CAG | ATC | ACG | GCG | AGG | ATC | GTG | GAC | CAG | TGC | GCC | AAC | GGC | GGG | CTC | 336 |
| Ala | Gln | Ile | Thr | Ala | Arg | Ile | Val | Asp | Gln | Cys | Ala | Asn | Gly | Gly | Leu | |
| | | | 100 | | | | 105 | | | | | 110 | | | | |

```
GAC  CTC  GAC  TGG  GAC  ACC  GTC  TTC  ACC  AAG  ATC  GAC  ACC  AAC  GGG  ATT       384
Asp  Leu  Asp  Trp  Asp  Thr  Val  Phe  Thr  Lys  Ile  Asp  Thr  Asn  Gly  Ile
     115                 120                      125

GGG  TAC  CAG  CAG  GGC  CAC  CTC  AAC  GTC  AAC  TAC  CAG  TTC  GTC  GAC  TGC       432
Gly  Tyr  Gln  Gln  Gly  His  Leu  Asn  Val  Asn  Tyr  Gln  Phe  Val  Asp  Cys
     130                 135                      140

CGC  GAC  TAGATTGTCT  GTGGATCCAA  GGCTAGCTAA  GAATAAAAGG  CTAGCTAAGC              488
Arg  Asp
145

TATGAGTGAG  CAGCTG                                                                  504
```

(2) INFORMATION FOR SEQ ID NO:11:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO:11:

```
Met  Ala  Ala  Arg  Leu  Met  Leu  Val  Ala  Ala  Leu  Leu  Cys  Ala  Ala  Ala
 1              5                    10                       15

Ala  Met  Ala  Thr  Ala  Gln  Gln  Ala  Asn  Asn  Val  Arg  Ala  Thr  Tyr  His
          20                     25                            30

Tyr  Tyr  Arg  Pro  Ala  Gln  Asn  Asn  Trp  Asp  Leu  Gly  Ala  Pro  Ala  Val
          35                     40                            45

Ser  Ala  Tyr  Cys  Ala  Thr  Trp  Asp  Ala  Ser  Lys  Pro  Leu  Ser  Trp  Arg
     50                      55                       60

Ser  Lys  Tyr  Gly  Trp  Thr  Ala  Phe  Cys  Gly  Pro  Ala  Gly  Pro  Arg  Gly
65                       70                      75                            80

Gln  Ala  Ala  Cys  Gly  Lys  Cys  Leu  Arg  Val  Thr  Asn  Pro  Ala  Thr  Gly
               85                      90                            95

Ala  Gln  Ile  Thr  Ala  Arg  Ile  Val  Asp  Gln  Cys  Ala  Asn  Gly  Gly  Leu
               100                     105                      110

Asp  Leu  Asp  Trp  Asp  Thr  Val  Phe  Thr  Lys  Ile  Asp  Thr  Asn  Gly  Ile
          115                     120                      125

Gly  Tyr  Gln  Gln  Gly  His  Leu  Asn  Val  Asn  Tyr  Gln  Phe  Val  Asp  Cys
     130                     135                      140

Arg  Asp
145
```

(2) INFORMATION FOR SEQ ID NO:12:

(i) SEQUENCE CHARACTERISTICS:
        (A) LENGTH: 515 base pairs
        (B) TYPE: nucleic acid
        (C) STRANDEDNESS: double
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: Hordeum vulgare (xi) SEQUENCE DESCRIPTION: SEQ ID NO:12:

```
CTGCAGGATC  CATGGCGGCA  CGCCTGATGC  TGGTGGCGGC  GCTGCTGTGC  GCGGCGGCGG       60

CGATGGCCAC  GGCGCAGCAG  GCGAACAACG  TCCGGGCGAC  GTACCACTAC  TACCGGCCGG      120
```

-continued

| | | | | | | |
|---|---|---|---|---|---|---|
| CGCAGAACAA | CTGGGACCTG | GGCGCGCCCG | CCGTGAGCGC | CTACTGCGCG | ACCTGGGACG | 180 |
| CCAGCAAGCC | GCTGTCGTGG | CGGTCCAAGT | ACGGCTGGAC | GGCGTTCTGC | GGCCCCGCCG | 240 |
| GCCCCGCGG | GCAGGCGGCC | TGCGGCAAGT | GCCTCCGGGT | GACCAACCCG | GCGACGGGGG | 300 |
| CGCAGATCAC | GGCGAGGATC | GTGGACCAGT | GCGCCAACGG | CGGGCTCGAC | CTCGACTGGG | 360 |
| ACACCGTCTT | CACCAAGATC | GACACCAACG | GGATTGGGTA | CCAGCAGGGC | CACCTCAACG | 420 |
| TCAACTACCA | GTTCGTCGAC | TGCCGCGACT | AGATTGTCTG | TGGATCCAAG | GCTAGCTAAG | 480 |
| AATAAAAGGC | TAGCTAAGCT | ATGAGTGAGC | AGCTG | | | 515 |

( 2 ) INFORMATION FOR SEQ ID NO:13:

( i ) SEQUENCE CHARACTERISTICS:
( A ) LENGTH: 585 base pairs
( B ) TYPE: nucleic acid
( C ) STRANDEDNESS: double
( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Hordeum vulgare ( x i ) SEQUENCE DESCRIPTION: SEQ ID NO:13:

| | | | | | | |
|---|---|---|---|---|---|---|
| CTGCAGGGAT | CCTATTTTA | CAACAATTAC | CAACAACAAC | AAACAACAAA | CAACATTACA | 60 |
| ATTACTATTT | ACAATTACAC | CATGGCGGCA | CGCCTGATGC | TGGTGGCGGC | GCTGCTGTGC | 120 |
| GCGGCGGCGG | CGATGGCCAC | GGCGCAGCAG | GCGAACAACG | TCCGGGCGAC | GTACCACTAC | 180 |
| TACCGGCCGG | CGCAGAACAA | CTGGGACCTG | GGCGCGCCCG | CCGTGAGCGC | CTACTGCGCG | 240 |
| ACCTGGGACG | CCAGCAAGCC | GCTGTCGTGG | CGGTCCAAGT | ACGGCTGGAC | GGCGTTCTGC | 300 |
| GGCCCCGCCG | GCCCCGCGG | GCAGGCGGCC | TGCGGCAAGT | GCCTCCGGGT | GACCAACCCG | 360 |
| GCGACGGGGG | CGCAGATCAC | GGCGAGGATC | GTGGACCAGT | GCGCCAACGG | CGGGCTCGAC | 420 |
| CTCGACTGGG | ACACCGTCTT | CACCAAGATC | GACACCAACG | GGATTGGGTA | CCAGCAGGGC | 480 |
| CACCTCAACG | TCAACTACCA | GTTCGTCGAC | TGCCGCGACT | AGATTGTCTG | TGGATCCAAG | 540 |
| GCTAGCTAAG | AATAAAAGGC | TAGCTAAGCT | ATGAGTGAGC | AGCTG | | 585 |